(12) United States Patent
Gray

(10) Patent No.: US 8,168,425 B2
(45) Date of Patent: *May 1, 2012

(54) EXPRESSION OF FACTOR IX IN GENE THERAPY VECTORS

(75) Inventor: John Trainor Gray, Memphis, TN (US)

(73) Assignee: St. Jude Children's Research Hospital, Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/198,328

(22) Filed: Aug. 4, 2011

(65) Prior Publication Data

US 2011/0287532 A1    Nov. 24, 2011

Related U.S. Application Data

(63) Continuation of application No. 11/575,669, filed as application No. PCT/US2005/032078 on Sep. 9, 2005, now Pat. No. 8,030,065.

(60) Provisional application No. 60/612,135, filed on Sep. 22, 2004.

(51) Int. Cl.
*C12N 15/00* (2006.01)

(52) U.S. Cl. .................................... 435/320.1; 536/24.1

(58) Field of Classification Search .................... None
See application file for complete search history.

(56) References Cited

U.S. PATENT DOCUMENTS

| 6,093,392 | A | 7/2000 | High et al. |
| 6,670,176 | B1 | 12/2003 | Samulski et al. |
| 8,030,065 | B2 * | 10/2011 | Gray .......................... 435/320.1 |
| 2002/0064812 | A1 | 5/2002 | Connelly et al. |
| 2003/0022378 | A1 | 1/2003 | Ehrhardt et al. |
| 2003/0077812 | A1 | 4/2003 | McArthur et al. |
| 2004/0009151 | A1 | 1/2004 | Kay et al. |
| 2004/0023333 | A1 | 2/2004 | Hauser et al. |
| 2004/0029106 | A1 | 2/2004 | Samulski et al. |

FOREIGN PATENT DOCUMENTS

| WO | WO 01/66149 | A2 | 9/2001 |
| WO | WO 01/92551 | A2 | 12/2001 |
| WO | WO 01/98482 | A2 | 12/2001 |
| WO | WO 02/064799 | A1 | 9/2002 |

OTHER PUBLICATIONS

Nakai, H., et al, "Extrachromosomal Recombinant Adeno-Associated Virus Vector Genomes are Primarily Responsible for Stable Liver Transduction In Vivo"; *Journal of Virology*, vol. 75, No. 15, Aug. 1, 2001, pp. 6969-6976.
Database Accession No. AX249946, "Sequence 4 from Patent WO0166149", Sep. 13, 2001; F.B.I. Hinxton U.K., XP002550494.
Database Accession No. ABS68099, Nov. 19, 2002, "Clotting Factor IX Construct pFIXABCD", Seldon, R.F., et al., XP002550495.
Database Accession No. AAI71010, Dec. 27, 2001, "Human Apolipoprotein E Gene Hepatic Locus Control Element", E.B.I. Hinxton U.K., XP002550496.
Database Accession No. AAI71009, Mar. 18, 2002, "Human Apolipoprotein E Gene Enhancer", C.H. Miao et al., XP002550497.
Database Accession No. AAI71006, Mar. 18, 2002, "Human Alpha1 Antitrypsin Promoter", E.B.I. Hinxton U.K., XP002550498.
Wang, Z, et al., "Rapid and highly efficient transduction by double-stranded adeno-associated virus vectors in vitro and in vivo," GeneTherapy 10:2105-2111 (2003).
McCarty, D.M., et al., "Adeno-associated virus terminal repeat (TR) mutant generates self-complementary vectors to overcome the rate-limiting step to transduction in vivo," Gene Therapy 10:2112-2118 (2003).
McCarty, D.M., et al., "Self-Complementary recombinant adeno-associated virus (scAAV) vectors promote efficient transduction independently of DNA synthesis" Gene Therapy 8:1248-1254 (2001).
Ziegler, R.J., et al., "AAV2 vector harboring a liver-restricted promoter facilitates sustained expressionof therapeutic levels of alpha-galactosidase A and the induction of immune tolerance in Fabry mice," Mol. Therap.9(2):231-240 (2004).
Miao, CH., et al., "Inclusion of the hepatic locus control region, an intron, and untranslated region increases and stabilizes hepatic factor IX gene expression in vivo but not in vitro," Mol Ther 1(6):522-532 (2000).
Haas et al., Current Biology (1996), vol. 6, No. 3, pp. 315-324.
Davidoff, A.M., "Comparison of the Ability of Adeno-associated Viral Vectors Pseudotyped with Serotype 2, 5, and 8 Capsid Proteins to Mediate Efficient Transduction of the Live in Urine and Nonhuman Primate Models," *Molecular Therapy*, 2005, 875-888, vol. 11(6), The American Society of Gene Therapy, U.S.
Gao, G., "Novel Adeno-associated Viruses from Rhesus Monkeys as Vectors for Human Gene Therapy," *Proceedings of the National Academy of Sciences of USA*, Sep. 3, 2002, 11854-11859, vol. 99(18).
Welch, M., "You're One in a Googol: Optimizing Genes for Protein Expression," *J.R. Soc. Interface*, Mar. 11, 2009, S467-S476, vol. 6(4).

* cited by examiner

*Primary Examiner* — Jim Ketter
(74) *Attorney, Agent, or Firm* — Alston & Bird LLP

(57) ABSTRACT

Two mechanisms are provided for improving the expression of Factor IX in gene therapy vectors. The first is the use of a specific Factor IX polynucleotide coding sequence designed for optimal expression. The second is the use of transcriptional regulatory regions minimized in size so that they can be used to express Factor IX, as well as any other gene of interest, in a size-constrained environment such as in a self complementary gene therapy vector system.

9 Claims, 1 Drawing Sheet

EXPRESSION OF FACTOR IX IN GENE THERAPY VECTORS

CROSS-REFERENCE TO RELATED APPLICATIONS

This application is a continuation of U.S. application Ser. No. 11/575,669, filed Mar. 21, 2007 which claims priority to PCT/US05/32078, filed Sep. 9, 2005 and U.S. Provisional Application No. 60/612,135, filed Sep. 22, 2004, each of which is incorporated by reference in their entirety.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of 407787seqlist.txt, a creation date of Jul. 28, 2011 and a size of 10.5 KB. The sequence listing filed via EFS-Web is part of the specification and is hereby incorporated in its entirety by reference herein.

FIELD OF INVENTION

This invention relates to the field of gene therapy generally and more specifically to the use of gene therapy vectors to deliver genes useful in the treatment of hemophilia and lysosomal storage disorders.

BACKGROUND

Hemophilia is a genetic X-linked recessive bleeding disorder caused by a deficiency of a blood clotting factor. There are two basic types of hemophilia; hemophilia A and hemophilia B. Hemophilia A is caused by a deficiency in the blood clotting factor known as Factor VIII and affects approximately 17,000 people in the U.S. Hemophilia B is caused by a deficiency in the blood clotting factor known as Factor IX and affects approximately one out of every 34,500 men. The clinical presentations for both hemophilias are characterized by episodes of spontaneous and prolonged bleeding. Patients frequently suffer joint bleeds which lead to disabling arthropathy. Current treatment is directed at stopping the bleeding episodes with intravenous infusions of plasma-derived clotting factors or, for hemophilia A, recombinant Factor VIII. However, therapy is limited by the availability of clotting factors, their short half-lives in vivo, and the high cost of treatment.

Gene therapy offers the promise of a new method for treating hemophilia. Both types of hemophilia are excellent theoretical candidates for gene therapy as each has a reasonably simple molecular pathology and should be remediable by the delivery of a single gene. Successful gene therapy for hemophilia requires sufficiently high levels of expression of the deficient factor to generate a therapeutic response.

Several groups of researchers have conducted research with gene therapy vectors designed to express Factor IX, but have not been able to achieve stable production of therapeutic levels of these factors in humans. Recently, self-complementary vectors have been used to increase heterologous gene expression by increasing transduction efficiency. See U.S. Patent Pub. No. 2004/0029106, Wang, Z. et al., "Rapid and highly efficient transduction by double-stranded adeno-associated virus vectors in vitro and in vivo", *Gene Therapy* 10: 2105-2111 (2003); McCarty, D. M. et al., "Adeno-associated virus terminal repeat (TR) mutant generates self-complementary vectors to overcome the rate-limiting step to transduction in vivo", *Gene Therapy* 10: 2112-2118 (2003); McCarty, D. M. et al, "Self-complementary recombinant adeno-associated virus (scAAV) vectors promote efficient transduction independently of DNA synthesis", *Gene Therapy* 8: 1248-1254 (2001). However, liver specific expression cassettes currently in use in AAV gene therapy exceed the capacity of these scAAV vectors. See Ziegler, R. J. et al., "AAV2 vector harboring a liver-restricted promoter facilitates sustained expression of therapeutic levels of alpha-galactosidase and the induction of immune tolerance in Fabry mice", *Mol. Therap.* 9(2): 231-240 (February 2004); Miao, C. H. et al., "Inclusion of the hepatic locus control region, an intron, and untranslated region increases and stabilizes hepatic factor IX gene expression in vivo but not in vitro", *Mol. Ther.* 1(6):522-32 (2000).

Therefore there remains a need for enhancing the production of human Factor IX in vivo using gene therapy vectors to achieve therapeutically effective levels.

SUMMARY OF THE INVENTION

The present invention comprises two basic components useful for improving the expression of Factor IX in gene therapy vectors. The first component is a specific Factor IX coding sequence (SEQ ID No. 1) designed for optimal expression of human Factor IX (SEQ ID No. 2) in a mammalian cell, particularly a human cell. Expression cassettes and gene therapy vectors containing this component are also provided.

The second component is a transcriptional regulatory control region useful in regulating the selective expression of genes including but not limited to human Factor IX in liver cells. This transcriptional regulatory control region consists essentially of a smaller version of a known liver specific enhancer and a known promoter, both of which have been reduced in size by the inventor while retaining their function. The nucleotide sequence of this transcriptional regulatory control region is provided in SEQ ID No. 3, with nucleotides 1-192 representing the enhancer region and nucleotides 193-447 representing the promoter region. This enhancer and promoter region can be used separately or together to regulate the expression of an operably linked nucleotide sequence such as a gene of interest or an antisense molecule. This transcriptional regulatory control region can be used in vectors with limited capacity for insertions, such as in self complementary gene therapy vectors. Use of this region in a self complementary vector allows this type of vector to be used to express human Factor IX. Expression cassettes and gene therapy vectors containing this component are also provided.

DESCRIPTION OF SEQUENCE LISTING

SEQ ID No. 1 is the nucleotide coding sequence for human Factor IX optimized for expression.

SEQ ID No. 2 is the amino acid sequence of human Factor IX encoded by SEQ ID No. 1.

SEQ ID No. 3 is the nucleotide sequence of the regulatory region useful in regulating the expression of Factor IX. Nucleotides 1-192 are derived from an Apolipoprotein E hepatic control region that acts as a liver specific enhancer. Nucleotides 193-447 are derived from a human alpha-1 antitrypsin promoter region. See Miao, C. H. et al., "Inclusion of the hepatic locus control region, an intron, and untranslated region increases and stabilizes hepatic factor IX gene expression in vivo but not in vitro", *Mol. Ther.* 1(6):522-32 (2000).

DETAILED DESCRIPTION OF INVENTION

Definitions

Figure 1:
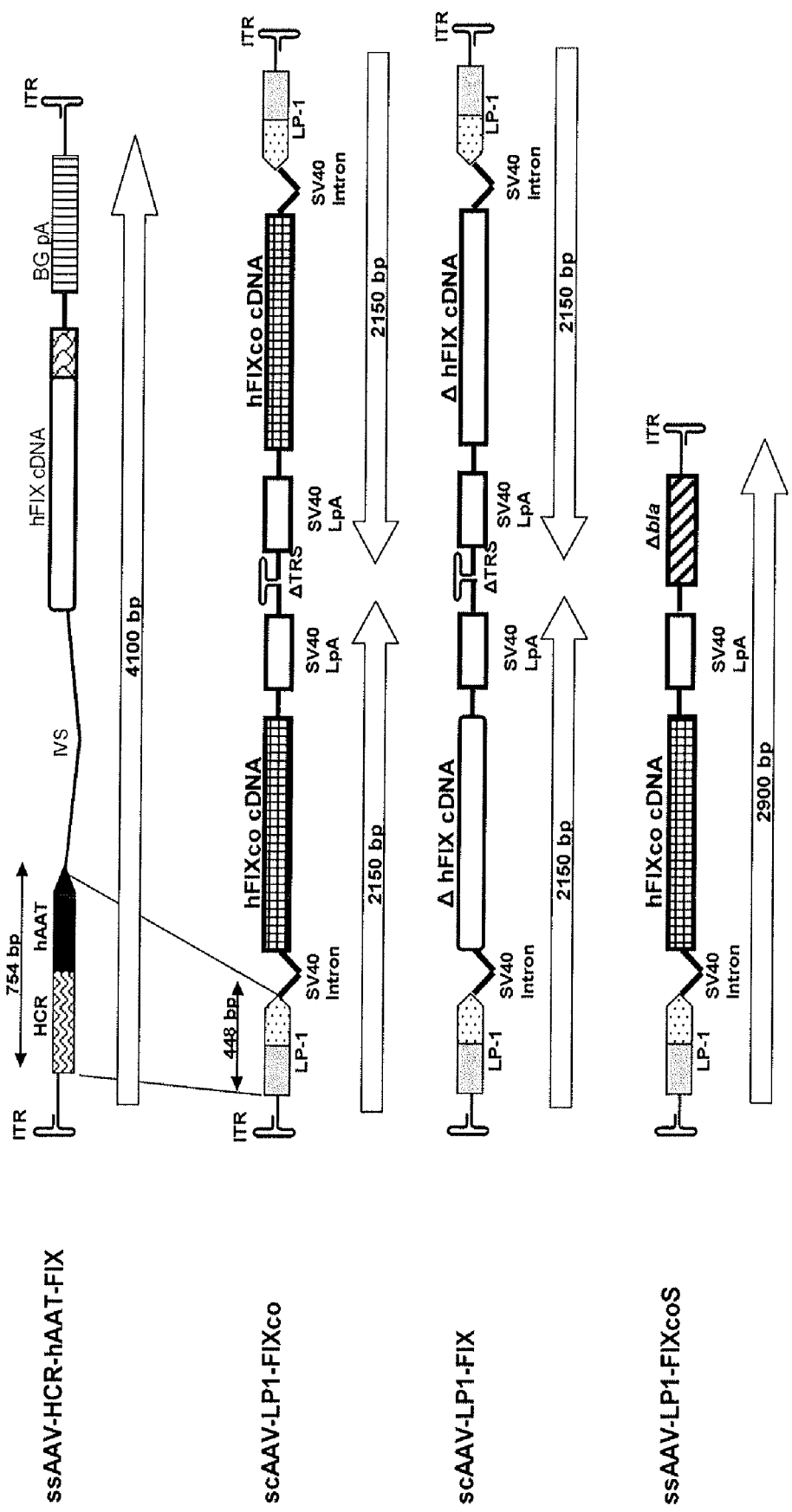
FIG. 1. Structure of rAAV hFIX vectors. Vectors described in Example 1 are shown schematically as they are packaged in the virion, with scAAV vectors shown as dimers. ssAAV-HCR-hAAT-FIX consisting of the human apolipoprotein E/C-I gene locus control region (HCR) and the human α1 antitrypsin promoter (hAAT), a chicken β actin/rabbit β globin composite intron (IVS), 1.6 kb human FIX cDNA (hFIX) and a bovine growth hormone polyadenylation signal (BGpA) flanked by the AAV internal terminal repeats (ITR shown as hairpin loop). Self complementary scAAV-LP1-hFIXco vector containing (i) the LP1 promoter consisting of core liver specific elements from HCR (base pairs 134 to 442 of Genbank record HSU32510) and hAAT (base pairs 1747 to 2001 Genbank record K02212) (ii) modified SV40 small t antigen intron (base pairs 4644 to 4552, Genbank record J02400) (iii) codon optimized hFIX (hFIXco) and (iv) SV40 late polyA (SV40 LpA, base pairs 2600 to 2733 GenBank J02400) and (v) a deleted 3' trs (Δtrs). scAAV-LP1-hFIX contains the wild type human FIX cDNA from which the 3' untranslated region has been deleted (ΔhFIX) instead of hFIXco. ssAAV-LP1-hFIXcoS has intact 5' and 3' ITR and in addition contains 760 bp of non-coding stuffer sequence from the β-lactamase (Δbla)

By "enhancer" is meant a polynucleotide that can stimulate promoter activity and thereby increase the level of expression of an operably linked gene of interest, antisense sequence, etc. relative to the level of expression that occurs in the absence of the enhancer. Enhancers may increase expression of operably linked sequences in a tissue specific or temporal manner.

By "expression cassette" is meant a complete set of control sequences including initiation, promoter and termination sequences which function in a cell when they flank a coding sequence in the proper reading frame. Expression cassettes frequently and preferably contain an assortment of restriction sites suitable for cleavage and insertion of any desired coding sequence.

By "gene of interest" is meant any coding sequence that is to be transcribed or transcribed and translated within a host organism. Such a gene of interest may include, but is not limited to, a gene that encodes a pharmaceutically active protein, for example growth factors, growth regulators, antibodies, antigens, their derivatives useful for immunization or vaccination and the like. Such proteins include, but are not limited to, interleukins, insulin, G-CSF, GM-CSF, hPG-CSF, M-CSF or combinations thereof, interferons, for example, interferon-.alpha., interferon-.beta., interferon-.pi., blood clotting factors, for example, Factor VIII, Factor IX, or tPA or combinations thereof. Such a gene of interest may also include, but is not limited to, an antisense DNA molecule or other DNA element intended to be transcribed but not translated.

By "gene therapy" is meant transcription or transcription and translation of exogenously supplied nucleic acid to prevent, palliate and/or cure a disease or diseases.

By "gene therapy vector" is meant a vector useful for gene therapy. Gene therapy vectors carry a gene of interest that is useful for gene therapy. The gene therapy vectors are able to be transferred to the cells of an animal, e.g., a human, and are able to express the gene of interest in such cells so as to effect gene therapy. The vector can be, e.g., chromosomal, non-chromosomal or synthetic. It can be, e.g., RNA or DNA. The vector can be, e.g., a plasmid, a virus or a phage. Preferred vectors include, e.g., retroviral vectors, adenoviral vectors, adeno-associated vectors, herpes virus vectors and Semliki Forest virus vector. A preferred retroviral vector is Murine Stem Cell Virus (MSCV), which is a variant of Moloney Murine Leukemia Virus (MoMLV).

By "operably linked" is meant that a DNA sequence coding for a polypeptide and regulatory sequence(s) (e.g. promoter, terminator, polyadenylation site, etc) are connected in such a way as to permit expression of the DNA coding sequence controlled by the regulatory sequence(s) when the appropriate molecules (e.g., transcriptional activator proteins) are bound to the regulatory sequence(s).

By "promoter" is meant a minimal sequence sufficient to direct transcription of an operably-linked gene of interest, antisense sequence, etc. Promoters provide the recognition for RNA polymerase and other transcriptional factors required for efficient transcription.

By "recombinant gene" is meant a combination of a DNA coding sequence and operably linked transcriptional regulatory regions which does not occur naturally.

By "transcriptional regulatory region" is meant a DNA sequence which induces or controls transcription of nucleotide sequences, particularly including protein coding sequences, with which it is operably linked.

DESCRIPTION OF THE INVENTION

In one aspect, the present invention comprises a polynucleotide encoding human Factor IX. This polynucleotide has the sequence set forth in SEQ ID No. 1 and expresses the human Factor IX protein having the amino acid sequence set forth in SEQ ID No. 2. This polynucleotide is designed for improved expression of human Factor IX when operably linked to appropriate regulatory elements such as a transcriptional promoter, termination signal, polyadenylation site, etc. and introduced into a mammalian cell. This polynucleotide is specifically designed for improved expression of human Factor IX in a human cell.

The polynucleotide set forth in SEQ ID No. 1 may be used to express human Factor IX in any desired expression cassette and/or vector using any desired transcriptional regulatory elements. Suitable vectors that may be used for this purpose include, but are not limited to, adeno-associated vectors (AAVs), self-complementary adeno-associated vectors (scAAVs), retroviruses, naked DNA and DNA:lipid mixtures.

Suitable transcriptional regulatory elements useful in expressing the Factor IX coding sequence of the invention include, but are not limited to, ApoE, ApoE HCR and human prothrombin enhancers as well as human serum albumin and h α-1 antitrypsin promoters. Particularly preferred are elements which regulate the specific expression of the Factor IX gene in the liver, such as the regulatory regions represented by SEQ ID No. 3, nucleotides 1-192 of SEQ ID No. 3 and nucleotides 193-447 of SEQ ID No. 3.

The present invention also includes polynucleotides that act as transcriptional regulatory control regions for operably linked nucleotides, particularly including antisense nucleotides and protein coding sequences. The transcriptional regulatory control regions of the invention include the contiguous sequence set forth in SEQ ID No. 3 as well as nucleotides 1-192 of SEQ ID No. 3 and nucleotides 193-447 of SEQ ID No. 3.

Nucleotides 1-192 of SEQ ID No. 3 are derived from a 320 nucleotide apolipoprotein E hepatic control region known to act as a liver specific enhancer. See Miao, C. H. et al., "Inclusion of the hepatic locus control region, an intron, and untranslated region increases and stabilizes hepatic factor IX gene expression in vivo but not in vitro", *Mol. Ther.* 1(6):522-32 (2000). This 192 polynucleotide of the invention can enhance liver specific expression of an operably linked polynucleotide in the same manner as the larger 320 polynucleotide Apolipoprotein E hepatic control region. This aspect of the invention includes an isolated transcriptional regulatory control region consisting of nucleotides 1-192 of SEQ ID No. 3 as well as expression cassettes and vectors having a liver specific enhancer region consisting essentially of nucleotides 1-192 of SEQ ID No. 3.

Nucleotides 193-447 of SEQ ID No. 3 are derived from a 408 nucleotide human alpha-1 antitrypsin promoter. See Miao, C. H. et al., Id. This 255 polynucleotide of the invention can promote expression of an operably linked polynucleotide in the same manner as the larger 408 polynucleotide human alpha-1 antitrypsin promoter. This aspect of the invention includes an isolated transcriptional regulatory control region consisting of nucleotides 193-447 of SEQ ID No. 3 as well as expression cassettes and vectors having a promoter region consisting essentially of nucleotides 193-447 of SEQ ID No. 3.

SEQ ID No. 3 represents a fusion of the liver specific enhancer derived from the apolipoprotein E hepatic control region and the promoter derived from human alpha-1 antitrypsin promoter. This fused enhancer-promoter transcriptional regulatory control region of the invention is significantly smaller than the fusion of the apolipoprotein E hepatic control region and human alpha-1 antitrypsin promoter disclosed in Miao, C. H. et al., Id.

The transcriptional regulatory control regions of the invention can be used to regulate the expression of any operably linked nucleotide or gene of interest in a mammalian cell, preferably in a human cell. This includes any gene of interest for which liver-specific expression is desired such as human Factor IX, human Factor VIII, and genes associated with lysosomal storage disorders [See Table 1 of U.S. Patent Application Publication No. 2002/0077292] such as protective protein/cathepsin A (PPCA), α-galactosidase, α-glucosidase, etc. The transcriptional regulatory control regions of the invention may be combined with other regulatory control regions in an expression cassette to achieve a desired pattern and level of expression of an operably linked gene of interest.

Since this regulatory region is smaller than known elements used to achieve the same pattern and level of expression, it can be used in place of such elements in those situations where the size limitations are imposed. For instance self-complementary adeno-associated vectors (scAAVs), which can be used to achieve higher expression of the heterologous genes they contain in the gene therapy context, can only accommodate recombinant genes or expression cassettes of a limited size of about 2.5 kb. By using the regulatory region of the invention in the expression cassette, larger coding sequences can be accommodated in the scAAV. In particular, the regulatory region of the invention is small enough to allow the expression of human Factor IX from an scAAV (see Example 1).

EXAMPLES

Example 1

Self complementary adeno-associated virus vectors containing a novel liver-specific human factor IX expression cassette enables highly efficient transduction of murine and nonhuman primate liver Summary Transduction with recombinant adeno-associated virus (AAV) vectors is limited by the need to convert its single-stranded (ss) genome to transcriptionally active double-stranded (ds) forms. For AAV-mediated hemophilia B (HB) gene therapy, we have overcome this obstacle by constructing a liver-restricted mini human factor IX (hFIX) expression cassette which can be packaged as complementary dimers within individual AAV particles. These self-complementary (sc) genomes rapidly anneal after uncoating to form stable, active ds-linear molecules. This unique property resulted in a 20 fold improvement in hFIX expression in mice over comparable ssAAV. Administration of only $1 \times 10^{10}$ scAAV particles lead to expression of biologically active hFIX at supraphysiological levels (8 IU/ml) and correction of the bleeding diathesis is HB mice. Importantly, therapeutic levels of hFIX (3-30% of normal) were achieved in nonhuman primates using a significantly lower dose of scAAV than required with ssAAV, even in macaques with pre-existing immunity to AAV. Hence, this novel vector represents an important advance for HB gene therapy.

Introduction

The liver is an important target for gene therapy of a variety of genetic disorders, one of which is FIB, a life threatening bleeding disorder that arises from mutations in the blood coagulation factor IX (FIX) gene. By maintaining plasma FIX levels above 1% of normal (>0.05 µg/ml) the incidence of spontaneous hemorrhage is dramatically reduced and so the therapeutic endpoint for HB gene therapy is modest (Nathwani, A. C. & Tuddenham, E. G., "Epidemiology of coagulation disorders", *Baillieres Clin. Haematol.* 5:383-439 (1992)). Currently, adeno-associated virus (AAV) vectors are the most promising for HB gene therapy and have been the focus of two recent clinical trials (Nathwani, A. C. et al., "Prospects for gene therapy of haemophilia", *Haemophilia.* 10: 309-318 (2004)).

Efficient transduction with AAV is, however, limited by the need to convert its single-stranded (ss) genome into transcriptionally active double-stranded (ds) forms in target cells because of its dependence on host cell mediated DNA synthesis of the leading strand (Fisher, K. J. et al., "Transduction with recombinant adeno-associated virus for gene therapy is limited by leading-strand synthesis", *J. Virol.* 70:520-532 (1996)) or annealing of complementary genomes derived from separate virions (Nakai, H. et al., "Annealing of complimentary single stranded genomes and subsequent intermolecular joining is the mechanism of stable In Vivo liver transduction by recombinant adeno-associated virus vectors", *Mol. Ther.* 1[5]: S125-S126 (2000)(Abstract)). Co-infection with adenovirus (Weitzman, M. D. et al., "Recruitment of wild-type and recombinant adeno-associated virus into adenovirus replication centers" *J. Virol.* 70: 1845-1854 (1996)) or priming the target tissues with genotoxic agents (Alexander, I. E. et al., "DNA-damaging agents greatly increase the transduction of nondividing cells by adeno-associated virus vectors", *J. Virol.* 68: 8282-8287 (1994); Mah, C. et al., "Adeno-associated virus type 2-mediated gene transfer: role of epidermal growth factor receptor protein tyrosine kinase in transgene expression", *J. Virol.* 72: 9835-9843 (1998)) can enhance ds transgene formation but the clinical utility of these approaches is limited by potential toxicity.

Rapid uncoating of the viral genome, as recently described with AAV8 vectors, allows efficient annealing of the ssAAV provirus to form double-stranded genomes. This unique biological property is responsible for the 10-100 fold higher transduction of the liver with rAAV8 when compared to AAV2 vectors in murine models (Davidoff, A. M. et al. Comparison of the ability of adeno-associated viral vectors pseudotyped with serotype 2, 5 and 8 capsid proteins to mediate efficient transduction of the liver in murine and non-human primate models. Mol. Ther. 11(6): 875-888 (2005); Gao, G. P. et al., "Novel adeno-associated viruses from rhesus monkeys as vectors for human gene therapy", *Proc. Natl. Acad. Sci. U. S. A* 99:11854-11859 (2002); Thomas, C. E. et al., "Rapid uncoating of vector genomes is the key to efficient liver transduction with pseudotyped adeno-associated virus vectors", *J. Virol.* 78: 3110-3122 (2004)). Even so, almost $10^{13}$ AAV8 vector particles are required to achieve 100% hepatocyte transduction in mice, a level that is required for successful gene therapy of some metabolic disorders of the liver (Nakai, H. et al., "Unrestricted hepatocyte transduction with adeno-associated virus serotype 8 vectors in mice", *J. Virol,* 79: 214-224 (2005)).

This high vector dose is problematic because it may: 1) cause hepatocellular toxicity in humans as observed in the recently concluded Phase I/II study (High, K. et al., "Human Immune Responses to AAV-2 Capsid May Limit Duration of Expression in Liver-Directed Gene Transfer in Humans with Hemophilia B", *Blood* 104: 121a (2004; Abstract)), 2) result in a broader tissue distribution of vector (Nathwani, A. C. et al., "Factors influencing in-vivo transduction by recombinant adeno-associated viral vectors expressing the human factor IX cDNA", *Blood* 97: 1258-1265 (2001)), 3) elicit stronger anti-capsid immunity due to the large viral load, and 4) put a tremendous burden on vector production. Needed, therefore, are novel strategies that can enhance liver transduction efficiency beyond that achieved with rAAV8 vectors, thereby allowing the use of lower vector doses to achieve therapeutic endpoints.

The ability to package double-stranded proviral DNA into individual AAV particles offers such an opportunity, as this would overcome a major limitation of this vector system. A number of groups have shown, using small reporter genes such as alkaline phosphatase or green fluorescent protein, that replicating provirus which is half the size of the wild type genome is naturally packaged as two complementary strands within a single AAV particle (McCarty, D. M. et al., "Adeno-associated virus terminal repeat (TR) mutant generates self-complementary vectors to overcome the rate-limiting step to transduction in vivo", *Gene Ther.* 10: 2112-2118 (2003); Wang, Z. et al., "Rapid and highly efficient transduction by double-stranded adeno-associated virus vectors in vitro and in vivo", *Gene Ther.* 10: 2105-2111 (2003); Hirata, R. K. & Russell, D. W., "Design and packaging of adeno-associated virus gene targeting vectors", *J. Virol.* 74. 4612-4620 (2000); Yang, G. S. et al., "Virus-mediated transduction of murine retina with adeno-associated virus: effects of viral capsid and genome size", *J. Virol.* 76: 7651-7660 (2002)). This enhances the efficiency with which transcriptionally active ds molecules are formed and has been shown to increase the transduction efficiency of hepatocyte, muscle and retina by 10-100 fold.

scAAV vectors however remain largely untested in large outbred animal models with respect to efficacy and toxicity. In addition, their smaller packaging capacity (~2.5 kb) has limited their use for clinical gene therapy despite recent endeavors to improve the efficiency with which the AAV genome is packaged as dimmers (McCarty, D. M. et al., Wang, Z. et al., infra).

Using hemophilia B gene therapy as a model, we have overcome this obstacle by constructing a novel mini-hFIX expression cassette on a modified AAV2 vector backbone that can be efficiently packaged as a tail-to-tail dimer in scAAV vectors. These vectors when critically evaluated in a murine model of HB and in large outbred nonhuman primates demonstrated significantly higher potency than their single-stranded counterparts. Indeed expression of hFIX at therapeutic levels was observed in nonhuman primates using vectors doses that proved to be subtherapeutic in the recently conducted Phase I/II study of AAV2 vectors in patients with severe HB (High, K. et al. infra). Hence scAAV vectors provide a promising approach for gene therapy of HB and other disorders affecting the liver.

Results

Construction and characterization of mini hFIX expression cassettes

Our previously described 4123 bp ssAAV-HCR-hAAT-hFIX liver-restricted expression cassette was modified (FIG. 1) to create a more compact (2.1 kb) hFIX expression cassette (scAAV-LP1-hFIXco) that met the packaging requirements of scAAV, while maintaining liver-restricted expression (Miao, C. H. et al., "Inclusion of the hepatic locus control region, an intron, and untranslated region increases and stabilizes hepatic factor IX gene expression in vivo but not in vitro", *Mol. Ther.* 1: 522-532 (2000); Davidoff, A. M. et al., "Purification of recombinant adeno-associated virus type 8 vectors by ion exchange chromatography generates clinical grade vector stock", *Journal of Virological Methods* 121[2]: 209-215 (2004)). Modifications included targeted deletions from the HCR and hAAT elements based on an analysis of liver transcription factor binding sites (Transfac), switching to smaller SV40 intronic and polyadenylation sequences, and deletion of the FIX 3' untranslated (3'UTR) sequences as mutations in this region have not been described in HB patients (Green, P. M. et al., "Mutation rates in humans. I. Overall and sex-specific rates obtained from a population study of hemophilia B" *Am. J. Hum. Genet.* 65: 1572-1579 (1999)). Additionally, the hFIX coding sequence was modified by using a subset of codons most frequently found in highly expressed eukaryotic genes ("codon optimization"), and then adjusted to reduce the potential for inappropriate splicing and CpG methylation to augment transgene expression. A second construct was made in which the wild-type hFIX coding sequence without the 3'UTR was used (scAAV-LP1-hFIX).

In both of these vectors the downstream terminal resolution site (trs) was deleted to enhance the formation of tail-to-tail self complementary dimmers (Wang, Z. et al. infra.) For comparison, an almost identical single-stranded vector was made (ssAAV-LP1-hFIXcoS) in which both trs were intact. This vector contained, in addition, 760 bp of noncoding stuffer sequence at the 3' end thereby exceeding the packaging limit for scAAV. Importantly, the ability of these new constructs to drive hFIX expression from transfected HuH7 cells was similar to that of the parent vector plasmid, AAV-HCR-hAAT-hFIX. Additionally, the yield of scAAV vectors, when pseudotyped with serotype 5 or 8 capsid protein, was in the range of $1–3\times10^4$ particles/cell, which is comparable to single-stranded counterparts, thus confirming that deletion of a single trs does not compromise viral replication or packaging (Wang, Z. et al. infra.; Samulski, R. J. et al., "Rescue of adeno-associated virus from recombinant plasmids: gene correction within the terminal repeats of AAV", *Cell* 33: 135-143 (1983)). Alkaline agarose gel electrophoresis confirmed that the scAAV2/8-LP1-hFIXco genome was consistently packaged as a dimer of ~4.6 kb whilst ssAAV2/8-LP1-hFIXcoS and ssAAV2/8-HCR-hAAT-hFIX were predominantly packaged as ss-genomes.

scAAV Vectors Mediate Substantially Higher Transduction of the Murine Liver

To establish the relationship between transduction efficiency and vector dose, different doses of scAAV2/8-LP1-hFIXco or ssAAV2/8-HCR-hAAT-hFIX vectors were administered via tail vein to male C57B1/6 mice and plasma hFIX levels assessed at 6 weeks. A relatively linear vector dose-transgene expression profile was observed with both types of vectors with no evidence of saturation kinetics at the doses examined. This is consistent with previous reports with single stranded serotype 8 vectors (Davidoff, A. M. et al. infra. (2005); Nakai, H. et al., 2005 infra.) At all vector doses evaluated, steady state hFIX levels were consistently higher for scAAV2/8-LP1-hFIXco by approximately 20-fold over the single-stranded counterparts. When $1 \times 10^{11}$ scAAV2/8-LP1 hFIXco vector particles were injected into the tail vein of mice, supraphysiological levels of hFIX ($151 \pm 43$ µg/ml) were observed, as compared to $5 \pm 0.5$ µg/ml with an equivalent dose of ssAAV2/8-HCR-hAAT-hFIX.

We next compared transduction efficiency of our scAAV with AAV-hF.IX16, the single-stranded vector that was used in the recent clinical trial (High, K. et al., "Immune response to AAV and to factor IX in a Phase I study of AAV-mediated liver directed gene transfer for hemophilia B", *Mol. Ther.* 9: S383-S384 (2004)(Abstract)). This vector, which in addition to the HCR-hAAT regulatory complex also contains a 1.4 kb region from the first intron of the hFIX gene and has been shown to mediate high levels of hFIX in animal models after liver targeted delivery (High, K. et al., *Blood*, infra.; McCarty, D. M. et al, infra.; High, K. et al. *Mol. Ther.*, infra) In our direct comparison, steady state hFIX expression after tail vein administration of $2.5 \times 10^{10}$ serotype 8 pseudotyped AAV-hF.IX16 particles was $10 \pm 0.5$ µg/ml which is 3 fold lower than that achieved with an equivalent dose of scAAV2/8-LP1-hFIXco ($29 \pm 2$ µg/ml P<0.001 by Student t-test). Hence, despite substantial engineering and size reduction, our scAAV-FIX vector appears to offer an advantage over the most optimised ssAAV-FIX vector in mice.

Immunohistochemical staining of murine liver after tail vein administration of $1 \times 10^{11}$ scAAV2/8-LP1-hFIXco showed expression of hFIX in 25% of hepatocytes at day 7 which increased to over 90% by 6 weeks. This is substantially higher than that observed with an equivalent dose of ssAAV2/8 vector (Davidoff, A. M. et al. infra. (2005); Nakai, H. et al., 2005 infra). Tail vein administration of $1 \times 10^{11}$ scAAV-LP1-hFIXco particles pseudotyped with serotype 5 capsid resulted in peak hFIX levels of $8.3 \pm 2$ µg/ml in male C57B1/6 mice, which is about 2 logs greater than previously reported for ssAAV2/5-HCR-hAAT-hFIX vectors (Davidoff, A. M. et al. infra. (2005)), but ~20-fold lower than the levels achieved with an equivalent dose of scAAV2/8 vector. Similar differences have been noted previously with ssAAV vectors thus indicating that capsid proteins and not genomic conformation are primarily responsible for the inferior transduction observed with AAV5 vectors in murine models (Davidoff, A. M. et al. infra. (2005)).

The transgene expression profile was next assessed following tail vein administration of $2 \times 10^9$ vector genomes (vg), a dose below the transduction threshold for ssAAV2 vectors (Nathwani, A. C. et al., "Factors influencing in-vivo transduction by recombinant adeno-associated viral vectors expressing the human factor IX cDNA", *Blood* 97: 1258-1265 (2001); Nakai, H. et al., "A limited number of transducible hepatocytes restricts a wide-range linear vector dose response in recombinant adeno-associated virus-mediated liver transduction", *J. Virol.* 76: 11343-11349 (2002)). Surprisingly, there was no difference in expression kinetics between vectors containing ssAAV2/8 (HCR-hAAT-hFIX and LP1-hFIXcoS) or scAAV2/8 (LP1-hFIXco and LP1-hFIX) genomes, with hFIX being detectable within a week but reaching peak levels after a lag phase of 4 weeks. There then followed a decline in transgene expression in all 4 cohorts of between 40-70% over a period of 20 weeks prior to stabilization, similar to that previously observed with ssAAV2/8 vectors (Davidoff, A. M. et al. infra. (2005); Nakai, H. et al., 2005 infra). Peak levels of hFIX in ssAAV2/8-HCR-hAAT-hFIX transduced mice were $0.052 \pm 0.01$ xg/ml, consistent with our previous report (Davidoff, A. M. et al. infra. (2005)). Similar levels of hFIX ($0.076 \pm 0.03$ µg/ml) were achieved in the ssAAV2/8-LP1-hFIXcoS cohort. In contrast, tail vein administration of $2 \times 10^9$ scAAV2/8-LP1-hFIXco vector particles resulted in MIX expression at almost 100% of physiological levels ($3.2 \pm 0.15$ µg/ml). This difference in transgene expression between single-stranded and scAAV was highly significant (p<0.001, by one way ANOVA analysis). Expression of hFIX in the scAAV2/8-LP1-hFIX cohort was four-fold lower ($0.77 \pm 0.03$ µg/ml). Transgene copy number in the liver of selected animals from the scAAV2/8-LP1-hFIXco and scAAV2/8-LP1-hFIX cohorts was similar (7.3 and 6.2 copies per diploid genome[c/dg] respectively) indicating that expression of the hFIX gene in mice appears to be influenced by codon usage, when its 3'UTR is removed.

To confirm correction of phenotype with this vector, we injected either $1 \times 10^{10}$ (low-dose cohort, n=6) or $5 \times 10^{10}$ (high-dose cohort, n=4) scAAV2/8 LP1-hFIXco into the tail vein of 129/sv HB mice that have a large deletion within exon 8 of the murine FIX gene (Wang, L. et al., "A factor IX-deficient mouse model for hemophilia B gene therapy", *Proc. Natl. Acad. Sci. U.S. A* 94: 11563-11566 (1997)). Peak hFIX:C levels as determined by a one-stage clotting assay were $8 \pm 0.7$ and $27 \pm 61$ U/ml in the low and high-dose cohorts respectively, significantly above background hFIX:C levels (0.03 U/mL) in untreated hemophiliac mice. There was complete concordance between hFIX:C and hFIX antigen levels in both cohorts of mice at all time points examined. Normal human plasma levels of FIX:C are defined as 1 IU/mL. Importantly all 6 untreated HB mice required wound cautery after tail vein puncture to achieve hemostasis whilst this was not necessary in the scAAV treated mice. Importantly, plasma thrombin-antithrombin complexes levels ($2.2 \pm 0.2$ µg/1) were not elevated, indicating that supraphysiological levels of biologically active hFIX do not induce a noticeable hypercoagulable state in HB mice. Finally, anti-hFIX antibodies were not detected in the scAAV treated HB mice at any stage after gene transfer.

Molecular Configuration and Biodistribution of scAAV Vector

Southern blot analysis of Hirt DNA extracted from the liver at 1 and 42 days after tail vein administration of $1 \times 10^{11}$ virions was performed to understand the mechanisms for the higher potency of scAAV vectors. At 24 hours, most of the scAAV2/8-LP1-FIXco genome was present as a double-stranded 2.1 kbp linear monomer, as confirmed by Pst I digestion which cuts ~500 bp from the 3'ΔITR to release a 1.8 kbp product. Even at this early time point, aside from supercoiled circles, an array of larger molecular forms including high molecular weight concatemers (HMWC~5%) were observed. At 42 days, supercoiled circular and concatameric forms predominated. Digestion with Pst I generated both head-to-head and head-to-tail concatemer fragment size in a ratio of 3:1 respectively. The circular forms, as expected, were resistant to digestion with plasmid-safe DNase.

To distinguish between transgene expression from integrated and extrachromosomal vector we induced hepatocellular regeneration by performing a two-thirds hepatectomy in HB mice 16 weeks after administration of $1 \times 10^{10}$ scAAV2/8-LP1-hFIXco. Though hemostasis was easily achieved, there was a sharp decline (~90%) in hFIX:C levels which did not recover despite complete restoration of liver cell mass within 4 weeks of surgery. In addition a concomitant decline in the vector copy number (~86%) was also observed post-hepatectomy indicating that extrachromosomal and not integrated scAAV genomes are primarily responsible for transgene expression.

Finally using a semiquantitative PCR assay scAAV genomes could be detected in all tissues examined 6 weeks after tail vein administration of scAAV2/8-LP1-hFIXco, with disproportionately higher levels of the transgene in the liver, as previously reported (Davidoff, A. M. et al. infra. (2005); Nakai, H. et al., 2005 infra). hFIX mRNA expression, however, was only detected in the liver by RT-PCR analysis. The specificity of the LP1 regulatory element was further assessed by direct intramuscular injection of $3 \times 10^{10}$ scAAV2/8-LP1-hFIXco. Despite efficient transduction, hFIX mRNA was absent by RT-PCR analysis of skeletal muscle suggesting that the LP1 regulatory element is not efficient at directing transgene expression in non-hepatic murine tissues.

Liver Targeted Delivery of Lower Doses of scAAV Mediate Expression of hFIX at Therapeutic Levels in Nonhuman Primates Based on extrapolation from murine studies, we have previously effected efficient transduction of the macaque liver with a standard dose of $4 \times 10^{12}$ ssAAV vector/kg pseudotyped with serotype 2, 5 or 8 capsid (Davidoff, A. M. et al. infra. (2005); Nathwani, A. C. et al., "Sustained high-level expression of human factor IX (hFIX) after liver-targeted delivery of recombinant adeno-associated virus encoding the hFIX gene in rhesus macaques", *Blood* 100: 1662-1669 (2002)). A similar dose of AAV-hF.IX16 mediated transient expression of hFIX following liver directed delivery of serotype 2 vector in severe HB patients (Fligh, K. et al., *Mol. Ther.* infra.) Lower doses of ssAAV2 ($2 \times 10^{11}$ or $1 \times 10^{12}$ vg/kg) were ineffective in humans and generated inconsistent expression in animals (Davidoff, A. M. et al. infra. (2005); High, K. et al., *Mol. Ther.* infra.; Nathwani, A. C. et al., id.).

The higher potency of scAAV in mice prompted the evaluation of two lower doses of scAAV2/8-LP1-hFIXco in macaques. The first group of macaques (M1-sc and M2-sc) received $1 \times 10^{12}$ vp/kg of vector which was infused into the mesenteric vein. scAAV2/8-LP1-hFIXco was well tolerated without perturbation of serum interleukin 6 levels (<3 pg/ml) or liver transaminases (alanine aminotransferase<65 U/L) over a period of 6 weeks after gene transfer. Within 24 hours of vector administration hFIX was detectable at 0.25 and 1.2 µg/ml and continued to rise over a period of 2 weeks prior to reaching peak values of approximately 12% and 30% of physiologic in M1-sc and M2-sc respectively. In M1-sc, these levels were stably maintained for 9 weeks before being abrogated by anti-hFIX antibodies whose titer increased rapidly over a period of 4 weeks to reach a stable level of 15 BIAU/ml. The coagulation screen in this animal was normal which is consistent with selective targeting of hFIX and not its rhesus cognate by this antibody. Detailed epitope mapping studies demonstrated specific reactivity with the serine protease domain in the substrate-binding cleft of the hFIX protein, a region which harbors 6 of the 12 amino acid differences between hFIX and its rhesus cognate. Treatment with Rituximab and daily oral cyclosporine was commenced to eradicate the neutralizing anti-hFIX antibody. Within 4 weeks of the start of this regimen the inhibitor become undetectable and hFIX was once again detectable in plasma at the previous peak levels of 0.8±0.1 µg/ml.

Two additional macaques (M3-sc and M4-sc) received $4 \times 10^{11}$ vp/kg of scAAV2/8-LP1-hFIXco, which represents a log reduction of our standard dose. Steady state hFIX levels of 0.19 µg/ml (3.75% of normal) were achieved within 2 weeks of liver targeted administration of vector in M3-sc. Transgene expression in this animal has been stably maintained for the duration of the study (>6 months). The second macaque in this group (M4-sc) had a low, but detectable pre-existing anti-AAV8 antibody titer (3.4 compared to a range of 0.6-1.0 relative units respectively in M1, M2 and M3-sc). This macaque was not successfully transduced after liver targeted administration of $4 \times 10^{11}$ vg/kg, suggesting that even modest levels of pre-existing immunity was sufficient to block successful transduction of the liver. However, switching capsid proteins resulted in successful transduction in this animal when challenged with $1 \times 10^{12}$ vg/kg of scAAV2/5-LP1-hFIXco, despite high titers of anti-AAV8 antibodies (>27 relative units) at the time of vector administration. The kinetics of hFIX expression was identical to that observed in M1 and 2 sc given scAAV-2/8 with a rapid increase in expression to peak levels of 20% of normal within 2 weeks after vector administration. This contrasts with the finding in mice where scAAV2/5 was 20-fold less active than scAAV2/8.

Transgene copy number in rhesus liver at 1 month after liver targeted delivery of $1 \times 10^{12}$ vg/kg of scAAV2/8-LP1-hFIXco or scAAV2/5-LP1-hFIXco was 61 and 49 c/dg respectively. This compares favorably with our previous experience in macaques given a four fold higher dose ($4 \times 10^{12}$ vg/kg) of ssrAAV where the transgene copy number ranged between 2-40 c/dg (Davidoff, A. M. et al. infra. (2005); Nathwani, A. C. et al., "Sustained high-level expression of human factor IX (hFIX) after liver-targeted delivery of recombinant adeno-associated virus encoding the hFIX gene in rhesus macaques", *Blood* 100: 1662-1669 (2002)). In M3-sc which was transduced with $4 \times 10^{11}$ vg/kg of scAAV2/8-LP1-hFIXco the transgene copy number in the liver was 34 c/dg in M3-sc at one month but then declined to 16 c/dg by 6 months. However hFIX expression was stably maintained at 2-3% of normal over this period showing once again the discordance between transgene expression and copy number reported by us before (Davidoff, A. M. et al. infra. (2005); Nathwani, A. C. et al., id). Semi-quantitative PCR analysis demonstrated the presence of the provirus in all the tissues examined including the testis, although there was no clear relationship between vector spill-over and vector dose outside of the liver and spleen. Further analysis of the vector genome distribution at 6 months revealed a substantial decline in copy number in all the nonhepatic tissues including the testis in M3-sc implying non-germ cell transduction. RT-PCR analysis revealed the presence of the hFIX mRNA only in the liver, again confirming the fidelity of the expression cassette.

Discussion

In this study we report the design and systematic evaluation of a novel mini-hFIX expression cassette that is efficiently packaged as self complementary dimers in a single AAV virion. These novel vectors proved to be safe and highly potent in both murine and nonhuman primate models, highlighting the importance of the viral genome configuration in mediating efficient transduction of the liver. In mice, scAAV vector encoding hFIX mediated substantially higher levels of hFIX than possible with ssAAV containing a variety of different carefully optimized expression cassettes. Therapeutic levels of hFIX (3-30% of physiological) were achieved in large out-bred nonhuman primates using vector doses previously regarded as subtherapeutic in humans and animal models of hemophilia. The superiority of scAAV results from its distinct molecular fate within the liver as after uncoating the scAAV genome rapidly forms stable double-stranded, linear molecules which are efficiently converted to HMWC. Using a hepatocellular regeneration model we show that the majority of the scAAV genomes, like ssAAV, are maintained in the liver as extrachromosomal, not integrated, forms. Hence the risk of insertional mutagenesis with this vector system which is an important consideration for all gene therapy strategies is likely to be low and comparable with that of ssAAV.

Maintenance of hFIX expression in the therapeutic range over the lifetime of a patient with HB may require repeated administration of scAAV to compensate for loss of episomal viral genomes as a consequence of natural hepatocyte turnover. Indeed we observed a decline in scAAV transgenes in the liver of one of our macaques (M3-sc) over a period of 6 months after liver targeted delivery of 4×10" vg/kg. Repeated transduction with vectors based on the same serotype will, however, be blocked by capsid-specific antibodies even when using the more potent scAAV vector system. We show that this obstacle can be circumvented with scAAV vectors pseudotyped with capsid protein of an alternative serotype, thereby extending our previous observation in macaques with ssAAV (Davidoff, A. M. et al. infra. (2005)). An important observation in this context is the similar high transduction efficiency observed with scAAV vectors pseudotyped with either serotype 5 or 8 capsid in macaques. We have previously observed similar transduction efficiency with ssAAV vector pseudotyped with 2, 5 or 8 capsid proteins in nonhuman primates (Davidoff, A. M. et al. infra. (2005)). Our experience in macaques with scAAV contrasts markedly with the disparate transduction efficacy observed with these serotypes in mice where the selection of capsid proteins strongly influences hepatocyte gene transfer efficiencies. These species-specific differences in the biological properties of AAV which may be due to differences in distribution of AAV receptor or intracellular processing of vector highlight once again the importance of evaluating new vector systems in a context relevant to humans.

One of the macaques that received scAAV (M1-sc) developed neutralizing antibodies to hFIX, but this did not occur in other animals given the same dose and expressing transgene at a higher level (M2-sc and M3-sc). We have previously observed neutralizing antibodies in a few ssAAV-transduced macaques (Davidoff, A. M. et al. infra. (2005); Nathwani, A. C. et al., id.). Although it is unclear why antibodies occur in some animals and not others our study shows that species related epitope differences are likely to contribute to this humoral response to the transgene product and may not ultimately be a problem in humans. However the development of this humoral response is of some concern and mandates effective strategies that would overcome this complication in humans. We therefore evaluated a rituximab based regimen in our macaque that developed neutralizing anti-hFIX antibodies because of its efficacy at treating auto-antibody mediated diseases such as acquired hemophilia (Stasi, R. et al., "Selective B-cell depletion with rituximab for the treatment of patients with acquired hemophilia", *Blood* 103: 4424-4428 (2004)). The strong temporal relationship between the start of rituximab/cyclosporine treatment with the rapid decline and eventual loss of the neutralizing anti-hFIX antibody indicates that this regimen may prove useful in treating humoral responses to the transgene product that develop after AAV mediated gene transfer. Further studies are however required to substantiate this interesting observation.

In summary, scAAV vectors encoding hFIX represent a significant advance for gene therapy of HB and raise new hope for other disorders affecting the liver. This, the first study to systematically evaluate scAAV encoding a therapeutically relevant gene shows that this vector system is highly efficient at transducing the liver in mice and nonhuman primates. Therapeutic transgene expression was observed in non human primates using substantially lower vector doses which will favorably impact on safety of this vector system and will additionally ease pressure on vector production. This novel approach will likely have broad utility for treatment of a variety of acquired and inherited disorders.

Methods and Materials

AAV-hFIX vector production and purification: An scAAV backbone plasmid was constructed by ligating Msc I-Bsa I and Bsa I-Tsp45 I fragments from AAV2-HCR-hAAT-FIX (Davidoff, A. M. et al. infra. (2005)) to the Simian Virus 40 late polyA (SV40 LpA). The resulting plasmid contained the modified AAV2 backbone with an intact 5' terminal resolution site (trs) and a deleted 3' trs analogous to that described previously (McCarty, D. M. et al., (2003) infra; Wang, Z. et al., (2003) infra.). The LP1 enhancer/promoter was constructed using standard PCR methods with amplification of consecutive segments of the human apolipoprotein hepatic control region HCR (HCR) the human alpha-1-antitrypsin (hAAT) gene promoter including the 5' untranslated region and cloned upstream of a modified SV40 small t antigen intron (SV40 intron modified at positions 4582 [g to c], 4580 [g to c], 4578 [a to c], and 4561 [a to t] into the modified AAV-2 backbone (FIG. 1). The wild type hFIX cDNA without the 3' untranslated regions (UTR) region was PCR amplified from AAV-HCR-hAAT-hFIX (Davidoff, A. M. et al. infra. (2005)) and inserted downstream of the modified SV40 intron to make scAAV-LP1-hFIX. A codon optimized hFIX was generated using codons most frequently found in highly expressed eukaryotic genes (Haas, J. et al., "Codon usage limitation in the expression of HIV-1 envelope glycoprotein", *Curr. Biol.* 6: 315-324 (1996). This codon optimized hFIX was synthesized as oligonucleotides, assembled by ligation, PCR amplified and sequenced prior to cloning into the AAV-LP1 backbone to create scAAV-LP1-hFIXco. scAAV-LP1-hFIXcoS contained a reconstructed normal 3' trs and a 760 bp of stuffer non-coding sequence from the 13-lactamase gene inserted downstream of the SV40-LpA. ss and scAAV vectors were made by the transient transfection method described before (Davidoff, A. M. et al., (2004) infra.) using pAAV5-2 (Chiorini, J. A. et al., "Cloning and characterization of adeno-associated virus type 5", *J. Virol.* 73: 1309-1319 (1999)) or pAAV8-2 (Gao, G. P. et al., infra) packing plasmids to generate serotype 5 and 8 recombinant vector respectively.

AAV2/5 vectors were purified by the previously described mucin affinity chromatography techniques (Auricchio, A. et al., "A single-step affinity column for purification of serotype-5 based adeno-associated viral vectors", *Mol. Ther.* 4: 372-374 (2001)). AAV2/8 vectors were purified using our recently described ion exchange chromatography method (Davidoff, A. M. et al., (2004) infra.). Vector genome (vg) titers were determined by our previously described quantitative slot-blot method (Nathwani, A. C. et al., (2001) infra). Importantly, each scAAV particle was calculated as containing two copies of ss viral genomes. The purified vector stocks were consistently free of contamination with wt-AAV and cellular and adenoviral proteins as judged by our previously described methods ((Davidoff, A. M. et al., (2004) infra; Nathwani, A. C. et al., (2001) infra). To determine the molecular configuration of scAAV vectors, vector stock was incubated with an equal volume of sample loading buffer (60 mM NaOH, 2 mm EDTA, 20% Ficoll and 0.06% Bromocresol green) and separated on a 1% agarose gel containing 30 mM NaOH and 1 mM EDTA, transferred to nitrocellulose by Southern blotting and hybridised with a $^{32}$P-labelled 842 bp BstApI fragment from the scAAV-LP1-FIXco at 42° C. The intensity of the hybridization was determined using the STORM phosphorimager (Amersham Biosciences, Amersham, U.K).

Animal studies: All procedures were performed in accordance with institutional guidelines under protocols approved by the Institutional Biosafety Committee and the Institutional Animal Care and Use Committee at St Jude Children's Research Hospital and University of Tennessee, Memphis. All animal work carried out in the UK was performed under the authority of the UK Home Office Project and Personal Licenses regulations and was compliant with the guidelines of the University College and Imperial College ethical review committee. The HB mouse strain, based on 129/sv mice with disruption of the factor IX gene, was obtained from Inder Verma (Salk Institute, La Jolla, Calif.) (Wang, L. et al., "A factor IX-deficient mouse model for hemophilia B gene therapy", *Proc. Natl. Acad. Sci. USA* 94: 11563-11566 (1997)).

Tail vein administration of rAAV vector particles was performed in 7-10 week old male mice as described before (Nathwani, A. C. et al., (2001) infra.). A two thirds partial hepatectomy were performed at 16 weeks after tail vein administration of 1×10$^{10}$ scAAV2/8-LP1-hFIXco as previously described (Nakai, H. et al., "Extrachromosomal recombinant adeno-associated virus vector genomes are primarily responsible for stable liver transduction in vivo", *J. Virol.* 75: 6969-6976 (2001)). Four weeks later, at a time when the liver mass was fully reconstituted, the mice were sacrificed to harvest the liver. Captive bred male *Macaca mulatta* aged between 2.5 to 6.6 years and weighing between 1.6 and 7.6 kg were purchased from Covance Research Products, Inc. (Alice, Tex.) and housed in the dedicated primate facility at the University of Tennessee Health Science Center. Vector particles in phosphate buffered saline (PBS), were infused into the mesenteric circulation of male macaques, as described before (Nathwani, A. C. et al., "Sustained high-level expression of human factor IX (hFIX) after liver-targeted delivery of recombinant adeno-associated virus encoding the hFIX gene in rhesus macaques", Blood 100: 1662-1669 (2002)). The CBC, serum chemistry and coagulation profile were performed by ANTECH Diagnostics (Southaven, Miss.). Serum IL-6 levels were assessed using an IL-6 immunoassay kit (R&D Systems, Oxford, UK) as per manufacturer's instruction. To eradicate anti-hIX antibody in M1-sc treatment with Rituximab (250 mg/m$^2$, 2 doses at 3 weekly intervals) and daily oral cyclosporine (30-100 mg/kg/day adjustment to trough therapeutic levels:-100-500 ng/ml) was started approximately 23 weeks after gene transfer.

Determination of transduction efficiency and vector biodistribution: Human FIX levels in murine and rhesus samples were determined by ELISA according to the previously described methods (Nathwani, A. C. et al., id). The probability of statistical difference between experimental groups was determined by one-way ANOVA and paired student t test using GraphPad Prizm version 4.0 software (GraphPad, San Diago, Calif.). A one-stage assay for hFIX:C was performed as described previously (Waddington, S. N. et al., "Permanent phenotypic correction of hemophilia B in immunocompetent mice by prenatal gene therapy", Blood 104: 2714-2721 (2004)). Background hFIX:C levels in untreated hemophiliac mice were as expected below 0.03 U/mL. The baseline clotting time of untreated HB mice in this assay was 87.2±3 sec, and that of normal 129/sv mice was 74.8±3 sec. Thrombin-antithrombin levels were determined using the Enzygnost TAT kit (Dade-Behring, Milton Keynes, U.K.). Low molecular weight Hirt DNA was extracted from liver at varying time points after tail vein administration of scAAV-2/8 vector using our previously described method (Davidoff, A. M. et al., "Sex significantly influences transduction of murine liver by recombinant adeno-associated viral vectors through an androgen-dependent pathway", Blood 102: 480-488 (2003)). Undigested Hirt DNA (10 ug) or DNA digested with PstI (which cuts once within the FIX expression cassette) was separated on 1% agarose gel, transferred to nitrocellulose by Southern blotting and hybridised with a $^{32}$P-labelled 842 bp BstAPI LP1 fragment fragment at 42° C. The intensity of the hybridization was determined using the STORM phosphorimager and ImageQuant software (Molecular Dynamics, Sunnyvale, Calif.). To determine AAV transgene copy number, high molecular weight genomic DNA (10 ug) extracted from murine and macaque tissues samples, using our previously described method (Nathwani, A. C. et al *Blood* 100: 1662-1669 (2002); Nathwani, A. C. et al., *Blood* 97: 1258-1265 (2001)) was digested with either BsrDI or a combination of EcoRI and PstI and electrophoresed through a 0.8% agarose gel and transferred to a nylon membrane (Hybond-N+; Amersham Biosciences, Arlington Heights, Ill. and Amersham, U.K) and then hybridized and quantitated as described above. To evaluate the biodistribution of AAV-FIX vectors, 1 ug of genomic DNA extracted from various murine and macaque tissues was subjected to PCR using primers which amplified a 617 bp region of hFIXco as follows:

```
                                             (SEQ ID NO: 4)
    5' primer: 5' TTTCCTGATGTGGACTATGT 3'

(SEQ ID NO: 5)
    3' primer: 5' TCATGGAAGCCAGCACAGAACATG 3'
```

This process was described previously (Nathwani, A. C. et al., *Blood* 100: 1662-1669 (2002)). Integrity of DNA was determined by amplifying a 604 bp region of the murine or rhesus β-actin gene using previously described primers (Nathwani, A. C. et al., *Blood* 97: 1258-1265 (2001). To determine which organs expressed hFIXco, total RNA was isolated and subjected to the reverse transcription conditions in the presence or absence of reverse transcriptase as described before Nathwani, A. C. et al., id.) Human FIX expression in various formalin fixed, paraffin embedded tissue specimens were analyzed by immunohistochemstry as described before (Davidoff, A. M. et al. infra. (2005)).

Detection of anti-human FIX antibodies and anti-AAV antibodies: Plasma samples from macaques were screened for the presence of antibodies against hFIX using an ELISA described previously (Nathwani, A. C. et al., *Blood* 100: 1662-1669 (2002)). Additionally the positive samples were subjected to the Bethesda assay as described before (Nathwani, A. C. et al., *Blood* 100: 1662-1669 (2002)). An immunocapture assay was used to detect anti-AAV specific antibodies in rhesus plasma as described (Nathwani, A. C. et al., *Blood* 100: 1662-1669 (2002)). Neutralizing antibody titers were analyzed by determining the ability of rhesus serum to inhibit transduction of 293T cells by pseudotyped rAAV vector containing the CMV-GIL as previously described (Nathwani, A. C. et al., *Blood* 100: 1662-1669 (2002); Nathwani, A. C. et al., "Efficient gene transfer into human cord blood CD34+ cells and the CD34+CD38- subset using highly purified recombinant adeno-associated viral vector preparations that are free of helper virus and wild-type AAV", *Gene Ther.* 7: 183-195 (2000)).

Various publications, patent applications and patents are cited herein, the disclosures of which are incorporated by reference in their entireties.

That which is claimed:

1. An expression cassette comprising a transcriptional regulatory control region operably linked to a polynucleotide, wherein said transcriptional regulatory control region comprises SEQ ID NO: 3.

2. The expression cassette of claim 1, wherein said polynucleotide encodes human Factor IX.

3. The expression cassette of claim 2, wherein said polynucleotide encodes the sequence set forth in SEQ ID NO:1.

4. A vector comprising the expression cassette of claim 1.

5. A vector comprising the expression cassette of claim 2.

6. A vector comprising the expression cassette of claim 3.

7. The vector of claim 4, wherein the vector comprises an adeno-associated virus (AAV) vector.

8. The vector of claim 7, wherein the AAV vector comprises an AAV type 2 vector pseudotyped with AAV serotype 5 capsid protein.

9. The vector of claim 7, wherein the AAV vector comprises an AAV type 2 vector pseudotyped with AAV serotype 8 capsid protein.

* * * * *

```
                        SEQUENCE LISTING

<160> NUMBER OF SEQ ID NOS: 5

<210> SEQ ID NO 1
<211> LENGTH: 1386
<212> TYPE: DNA
<213> ORGANISM: Homo sapiens
<220> FEATURE:
<221> NAME/KEY: CDS
<222> LOCATION: (1)...(1386)

<400> SEQUENCE: 1 atg cag agg gtg aac atg atc atg gct gag agc cct ggc ctg atc acc        48
Met Gln Arg Val Asn Met Ile Met Ala Glu Ser Pro Gly Leu Ile Thr
1               5                   10                  15 atc tgc ctg ctg ggc tac ctg ctg tct gct gag tgc act gtg ttc ctg        96
Ile Cys Leu Leu Gly Tyr Leu Leu Ser Ala Glu Cys Thr Val Phe Leu
                20                  25                  30 gac cat gag aat gcc aac aag atc ctg aac agg ccc aag aga tac aac       144
Asp His Glu Asn Ala Asn Lys Ile Leu Asn Arg Pro Lys Arg Tyr Asn
            35                  40                  45 tct ggc aag ctg gag gag ttt gtg cag ggc aac ctg gag agg gag tgc       192
Ser Gly Lys Leu Glu Glu Phe Val Gln Gly Asn Leu Glu Arg Glu Cys
        50                  55                  60 atg gag gag aag tgc agc ttt gag gag gcc agg gag gtg ttt gag aac       240
Met Glu Glu Lys Cys Ser Phe Glu Glu Ala Arg Glu Val Phe Glu Asn
65                  70                  75                  80 act gag agg acc act gag ttc tgg aag cag tat gtg gat ggg gac cag       288
Thr Glu Arg Thr Thr Glu Phe Trp Lys Gln Tyr Val Asp Gly Asp Gln
                85                  90                  95 tgt gag agc aac ccc tgc ctg aat ggg ggc agc tgc aag gat gac atc       336
Cys Glu Ser Asn Pro Cys Leu Asn Gly Gly Ser Cys Lys Asp Asp Ile
            100                 105                 110 aac agc tat gag tgc tgg tgc ccc ttt ggc ttt gag ggc aag aac tgt       384
Asn Ser Tyr Glu Cys Trp Cys Pro Phe Gly Phe Glu Gly Lys Asn Cys
        115                 120                 125 gag ctg gat gtg acc tgc aac atc aag aat ggc aga tgt gag cag ttc       432
Glu Leu Asp Val Thr Cys Asn Ile Lys Asn Gly Arg Cys Glu Gln Phe
    130                 135                 140 tgc aag aac tct gct gac aac aag gtg gtg tgc agc tgc act gag ggc       480
Cys Lys Asn Ser Ala Asp Asn Lys Val Val Cys Ser Cys Thr Glu Gly
145                 150                 155                 160 tac agg ctg gct gag aac cag aag agc tgt gag cct gct gtg cca ttc       528
Tyr Arg Leu Ala Glu Asn Gln Lys Ser Cys Glu Pro Ala Val Pro Phe
                165                 170                 175 cca tgt ggc aga gtg tct gtg agc cag acc agc aag ctg acc agg gct       576
Pro Cys Gly Arg Val Ser Val Ser Gln Thr Ser Lys Leu Thr Arg Ala
            180                 185                 190 gag gct gtg ttc cct gat gtg gac tat gtg aac agc act gag gct gaa       624
Glu Ala Val Phe Pro Asp Val Asp Tyr Val Asn Ser Thr Glu Ala Glu
        195                 200                 205 acc atc ctg gac aac atc acc cag agc acc cag agc ttc aat gac ttc       672
Thr Ile Leu Asp Asn Ile Thr Gln Ser Thr Gln Ser Phe Asn Asp Phe
    210                 215                 220 acc agg gtg gtg ggg ggg gag gat gcc aag cct ggc cag ttc ccc tgg       720
Thr Arg Val Val Gly Gly Glu Asp Ala Lys Pro Gly Gln Phe Pro Trp
225                 230                 235                 240
```

```
caa gtg gtg ctg aat ggc aag gtg gat gcc ttc tgt ggg ggc agc att      768
Gln Val Val Leu Asn Gly Lys Val Asp Ala Phe Cys Gly Gly Ser Ile
            245                 250                 255 gtg aat gag aag tgg att gtg act gct gcc cac tgt gtg gag act ggg      816
Val Asn Glu Lys Trp Ile Val Thr Ala Ala His Cys Val Glu Thr Gly
        260                 265                 270 gtg aag atc act gtg gtg gct ggg gag cac aac att gag gag act gag      864
Val Lys Ile Thr Val Val Ala Gly Glu His Asn Ile Glu Glu Thr Glu
    275                 280                 285 cac act gag cag aag agg aat gtg atc agg atc atc ccc cac cac aac      912
His Thr Glu Gln Lys Arg Asn Val Ile Arg Ile Ile Pro His His Asn
290                 295                 300 tac aat gct gcc atc aac aag tac aac cat gac att gcc ctg ctg gag      960
Tyr Asn Ala Ala Ile Asn Lys Tyr Asn His Asp Ile Ala Leu Leu Glu
305                 310                 315                 320 ctg gat gag ccc ctg gtg ctg aac agc tat gtg acc ccc atc tgc att     1008
Leu Asp Glu Pro Leu Val Leu Asn Ser Tyr Val Thr Pro Ile Cys Ile
            325                 330                 335 gct gac aag gag tac acc aac atc ttc ctg aag ttt ggc tct ggc tat     1056
Ala Asp Lys Glu Tyr Thr Asn Ile Phe Leu Lys Phe Gly Ser Gly Tyr
        340                 345                 350 gtg tct ggc tgg ggc agg gtg ttc cac aag ggc agg tct gcc ctg gtg     1104
Val Ser Gly Trp Gly Arg Val Phe His Lys Gly Arg Ser Ala Leu Val
    355                 360                 365 ctg cag tac ctg agg gtg ccc ctg gtg gac agg gcc acc tgc ctg agg     1152
Leu Gln Tyr Leu Arg Val Pro Leu Val Asp Arg Ala Thr Cys Leu Arg
370                 375                 380 agc acc aag ttc acc atc tac aac aac atg ttc tgt gct ggc ttc cat     1200
Ser Thr Lys Phe Thr Ile Tyr Asn Asn Met Phe Cys Ala Gly Phe His
385                 390                 395                 400 gag ggg ggc agg gac agc tgc cag ggg gac tct ggg ggc ccc cat gtg     1248
Glu Gly Gly Arg Asp Ser Cys Gln Gly Asp Ser Gly Gly Pro His Val
            405                 410                 415 act gag gtg gag ggc acc agc ttc ctg act ggc atc atc agc tgg ggg     1296
Thr Glu Val Glu Gly Thr Ser Phe Leu Thr Gly Ile Ile Ser Trp Gly
        420                 425                 430 gag gag tgt gcc atg aag ggc aag tat ggc atc tac acc aaa gtc tcc     1344
Glu Glu Cys Ala Met Lys Gly Lys Tyr Gly Ile Tyr Thr Lys Val Ser
    435                 440                 445 aga tat gtg aac tgg atc aag gag aag acc aag ctg acc tga             1386
Arg Tyr Val Asn Trp Ile Lys Glu Lys Thr Lys Leu Thr *
450                 455                 460

<210> SEQ ID NO 2
<211> LENGTH: 461
<212> TYPE: PRT
<213> ORGANISM: Homo sapiens

<400> SEQUENCE: 2

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
```

85                  90                  95
Cys Glu Ser Asn Pro Cys Leu Asn Gly Gly Ser Cys Lys Asp Asp Ile
                100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Ala Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
        355                 360                 365

Leu Gln Tyr Leu Arg Val Pro Leu Val Asp Arg Ala Thr Cys Leu Arg
    370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
        435                 440                 445

Arg Tyr Val Asn Trp Ile Lys Glu Lys Thr Lys Leu Thr
450                 455                 460

<210> SEQ ID NO 3
<211> LENGTH: 447
<212> TYPE: DNA
<213> ORGANISM: Homo sapiens

<400> SEQUENCE: 3
ccctaaaatg ggcaaacatt gcaagcagca aacagcaaac acacagccct ccctgcctgc    60

```
tgaccttgga gctggggcag aggtcagaga cctctctggg cccatgccac ctccaacatc    120
cactcgaccc cttggaattt cggtggagag gagcagaggt tgtcctggcg tggtttaggt    180
agtgtgagag gggaatgact cctttcggta agtgcagtgg aagctgtaca ctgcccaggc    240
aaagcgtccg ggcagcgtag gcgggcgact cagatcccag ccagtggact tagcccctgt    300
ttgctcctcc gataactggg gtgaccttgg ttaatattca ccagcagcct cccccgttgc    360
ccctctggat ccactgctta aatacggacg aggacagggc cctgtctcct cagcttcagg    420
caccaccact gacctgggac agtgaat                                         447

<210> SEQ ID NO 4
<211> LENGTH: 20
<212> TYPE: DNA
<213> ORGANISM: Artificial Sequence
<220> FEATURE:
<223> OTHER INFORMATION: primer sequence

<400> SEQUENCE: 4
tttctcgatg tggactatgt                                                 20

<210> SEQ ID NO 5
<211> LENGTH: 24
<212> TYPE: DNA
<213> ORGANISM: Artificial Sequence
<220> FEATURE:
<223> OTHER INFORMATION: primer sequence

<400> SEQUENCE: 5
tcatggaagc cagcacagaa catg                                            24
```